US00PP16742P3

(12) United States Plant Patent
Solberg

(10) Patent No.: US PP16,742 P3
(45) Date of Patent: Jul. 4, 2006

(54) ***HOSTA* PLANT NAMED 'ORANGE MARMALADE'**

(50) Latin Name: *Hosta hybrida*
Varietal Denomination: Orange Marmalade

(76) Inventor: Robert M. Solberg, 66 Codys Way, Franklinton, NC (US) 27525

( * ) Notice: Subject to any disclaimer, the term of this patent is extended or adjusted under 35 U.S.C. 154(b) by 392 days.

(21) Appl. No.: 10/725,770

(22) Filed: Dec. 2, 2003

(65) Prior Publication Data

US 2005/0120451 P1 Jun. 2, 2005

(51) Int. Cl.
*A01H 5/00* (2006.01)

(52) U.S. Cl. ..... Plt./353
(58) Field of Classification Search ..... Plt./353
See application file for complete search history.

(56) References Cited

U.S. PATENT DOCUMENTS

PP11,286 P 3/2000 Falstad
PP12,119 P2 10/2001 Fransen
PP12,663 P2 5/2002 Heemskerk
PP13,080 P2 10/2002 Hansen

OTHER PUBLICATIONS

This and That: 2001, The *Hosta* Journal, vol. 32, No. 2, pp. 73–81, see pp. 77 and 78.

This and That: 2002, The *Hosta* Journal, vol. 33, No. 3, pp. 66–70, see p. 66.

What's in a *Hosta* Name? Part XXX, 2003, The *Hosta* Journal, vol. 34, No. 1, pp. 42–49, see p. 47.

*Primary Examiner*—Kent Bell
*Assistant Examiner*—Louanne Krawczewicz Myers
(74) *Attorney, Agent, or Firm*—Ladas & Parry LLP

(57) ABSTRACT

A distinct cultivar of *Hosta* plant named 'Orange Marmalade', characterized by its medium sized, puckered broadly ovate variegated leaves of moderate substance, said leaves emerging yellow centered with an irregular blue-green margin and having additional streaks of yellow or greenish yellow between the margin and leaf center with the center of leaves becoming light yellow or near white; and light lavender flowers positioned on straight scapes in mid-summer.

4 Drawing Sheets

Latin name: *Hosta hybrida.*
Varietal denomination: 'Orange Marmalade'.

BACKGROUND OF THE INVENTION

The present invention relates to a new and distinct cultivar of *Hosta* plant, botanically known as *Hosta hybrida* cultivar name, 'Orange Marmalade'.

The new cultivar was discovered by the inventor as a naturally occurring whole plant mutation of the non-patented *Hosta* cultivar, 'Paul's Glory', in April 2000, in a nursery in Chapel Hill, N.C., United States of America.

Asexual reproduction of the new cultivar by tissue culture in 2001 at Rochelle, Ill., United States of America has shown that the unique features of this new *Hosta* plant are stable and reproduced true to type in successive generations of asexual reproduction.

BRIEF SUMMARY OF THE INVENTION

Plants of the cultivar 'Orange Marmalade' have not been observed under all possible environmental and cultural conditions. The phenotype may vary with changes in environmental conditions such as temperature, light intensity, day length, amount and frequency of irrigation and/or fertilizer rate, without any variance in genotype.

The following traits have been repeatedly observed and are determined to be unique characteristics of 'Orange Marmalade'. These characteristics in combination distinguish the *hosta* as a new and unique cultivar.

1. Medium sized, puckered broadly ovate variegated leaves of moderate substance comprising a compact medium sized clump. Substance is equated to the new overall appearance of the thickness of the leaf. It is frequently measured by rubbing the leaf between the fingers and thumb. "Moderate substance" means that the leaf is not thin but feels substantial. However, it is not thick to be leathery.
2. Leaves emerge yellow centered with an irregular blue green margin, leaves having additional streaks of yellow or greenish yellow between the margin and leaf center, center of leaves becoming light yellow or near white, depending on the amount of direct sunlight, later in the season.
3. Light lavender flowers are positioned on straight scapes in midsummer.

The new *hosta* can be compared to its parent cultivar, 'Paul's Glory', not patented. Plants of the new *hosta* emerge brightly variegated compared to plants of the parent that emerge almost a solid blue color. The color of the center of the leaf of the new plant is lighter in color throughout the growing season and is more varied with streaks of yellow (9C to 9B) and green (144A) than are found in the leaf center of the parent plant (154D). The new *hosta* also makes a smaller, more compact clump with shorter flower scapes when compared to 'Paul's Glory'.

BRIEF DESCRIPTION OF THE PHOTOGRAPHS

The accompanying colored photographs illustrate the overall appearance of the new *Hosta*, showing the colors as true as it is reasonably possible to obtain in color reproductions of this type. Colors in the photographs may differ slightly from the color value cited in the detailed botanical description, which accurately describe the actual colors in the new *Hosta*.

DETAILED DESCRIPTION OF THE INVENTION

Figure 1:
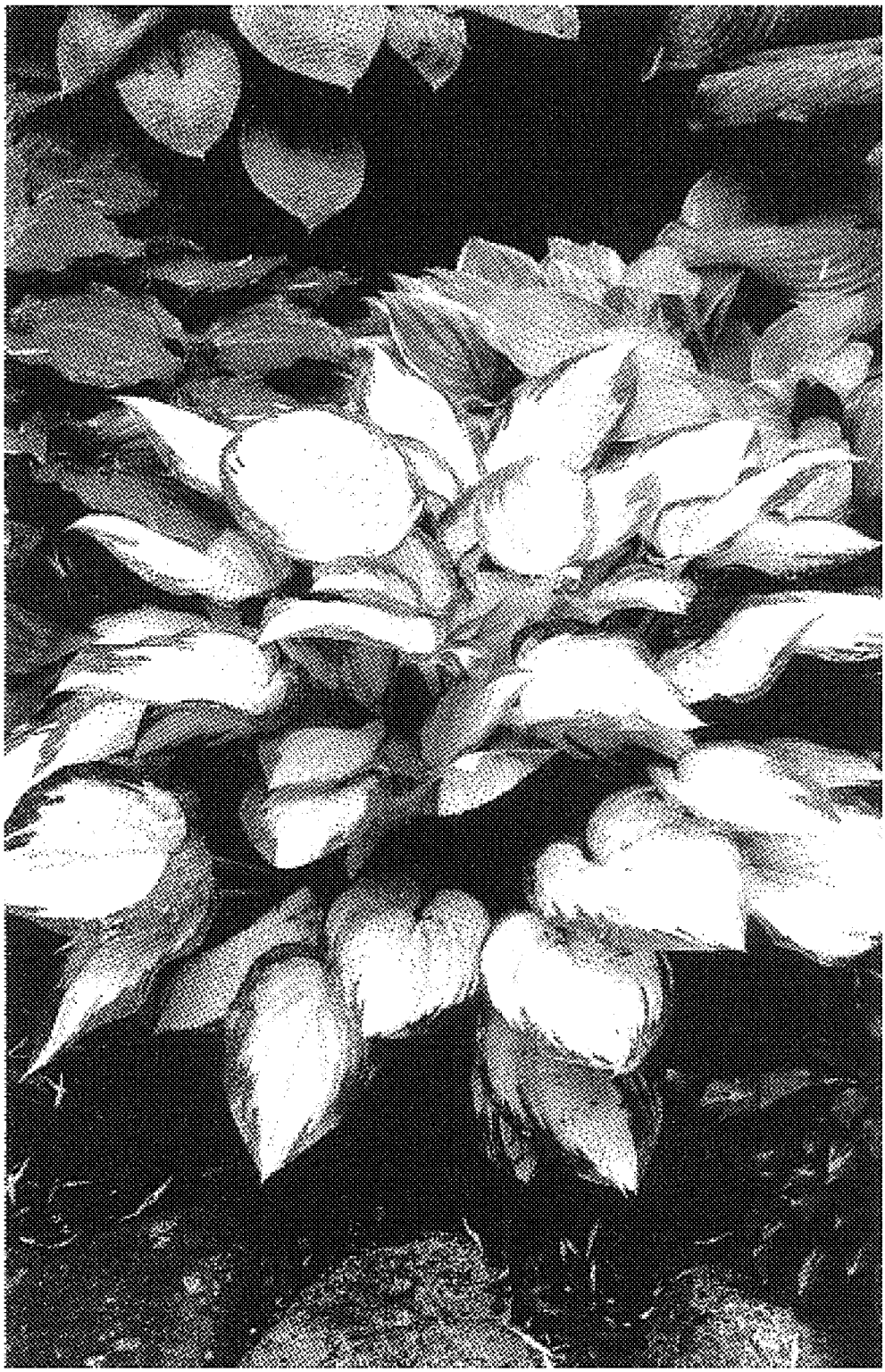
FIG. 1 shows the plant at mid-season with brightly variegated color.
Figure 2:
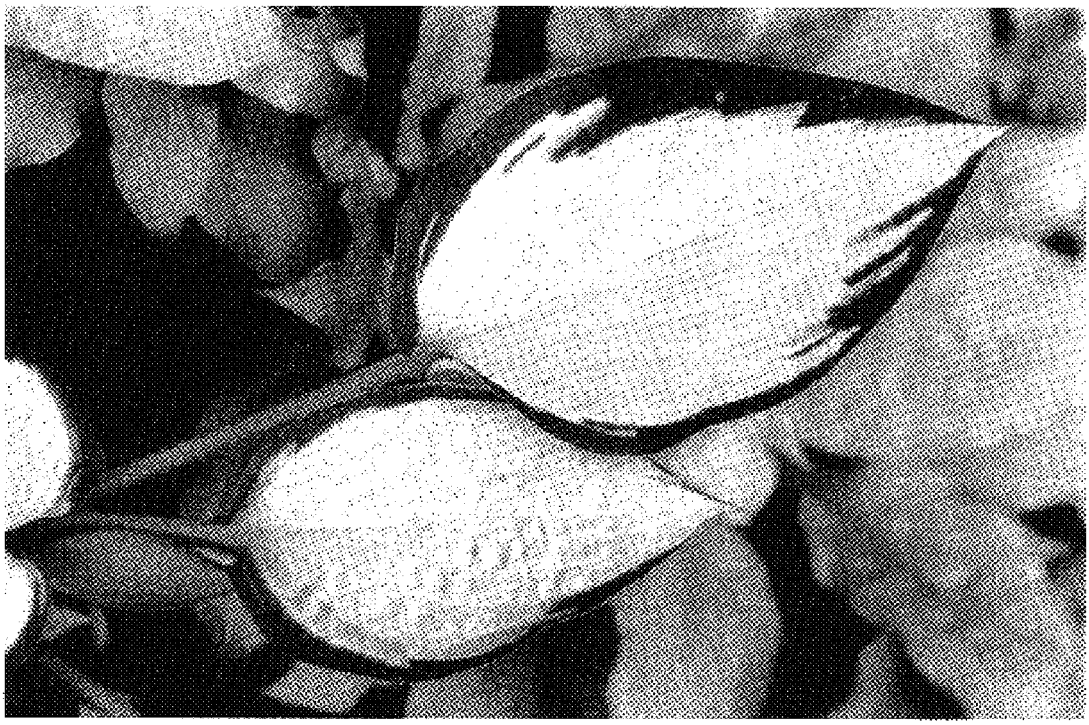
FIG. 2 shows a comparison of an early color leaf on the bottom and a mid-season color of the leaf on the top.
Figure 3:
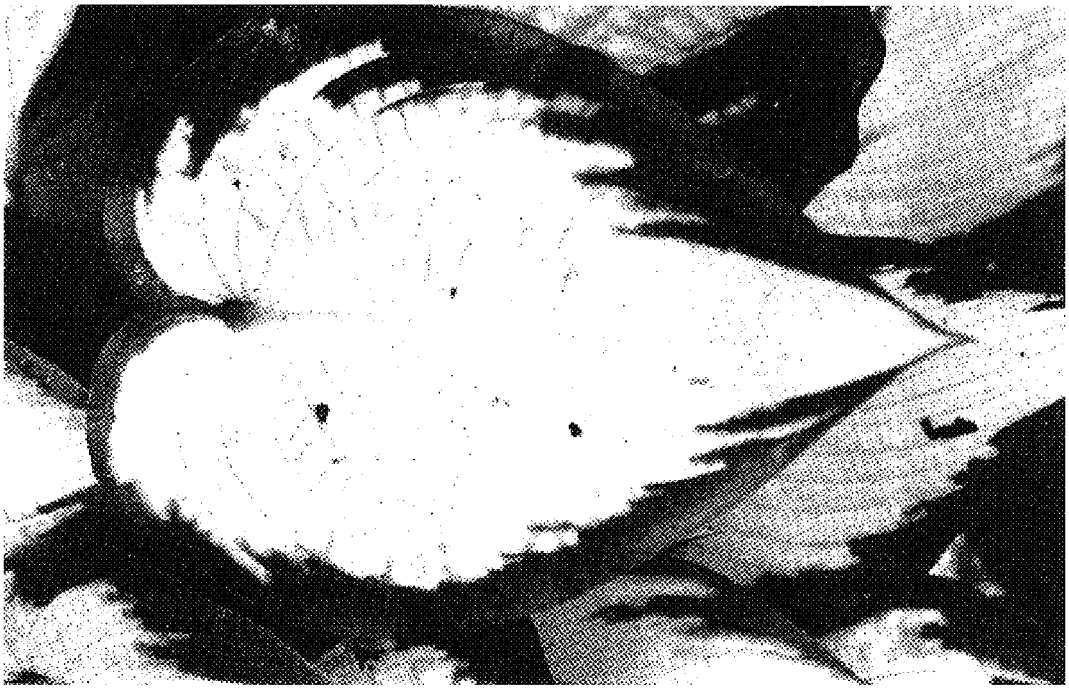
FIG. 3 shows a close-up photograph of the late season color of the leaf.
Figure 4:
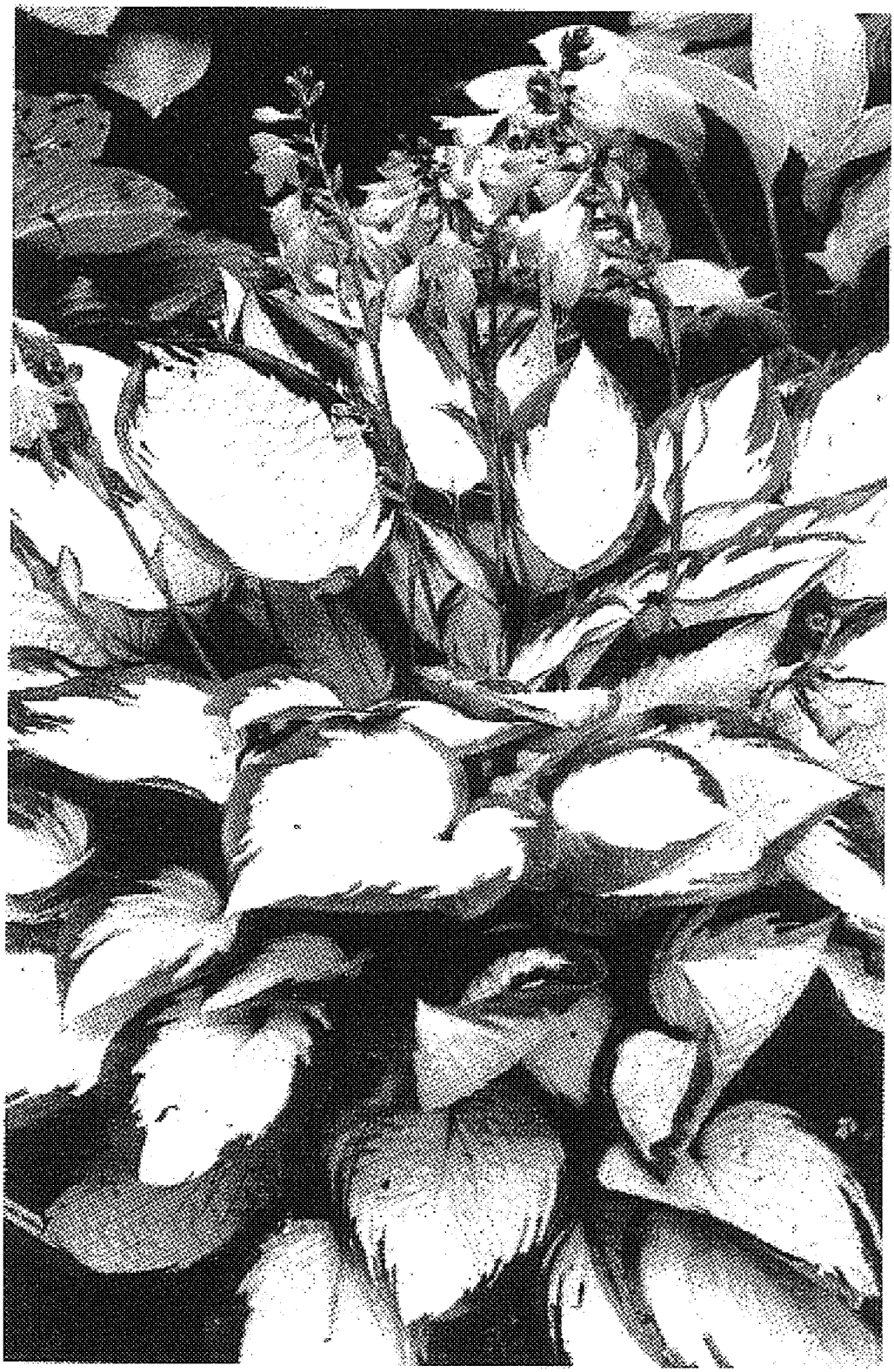
FIG. 4 shows the late season flowering plant.
Figure 5:
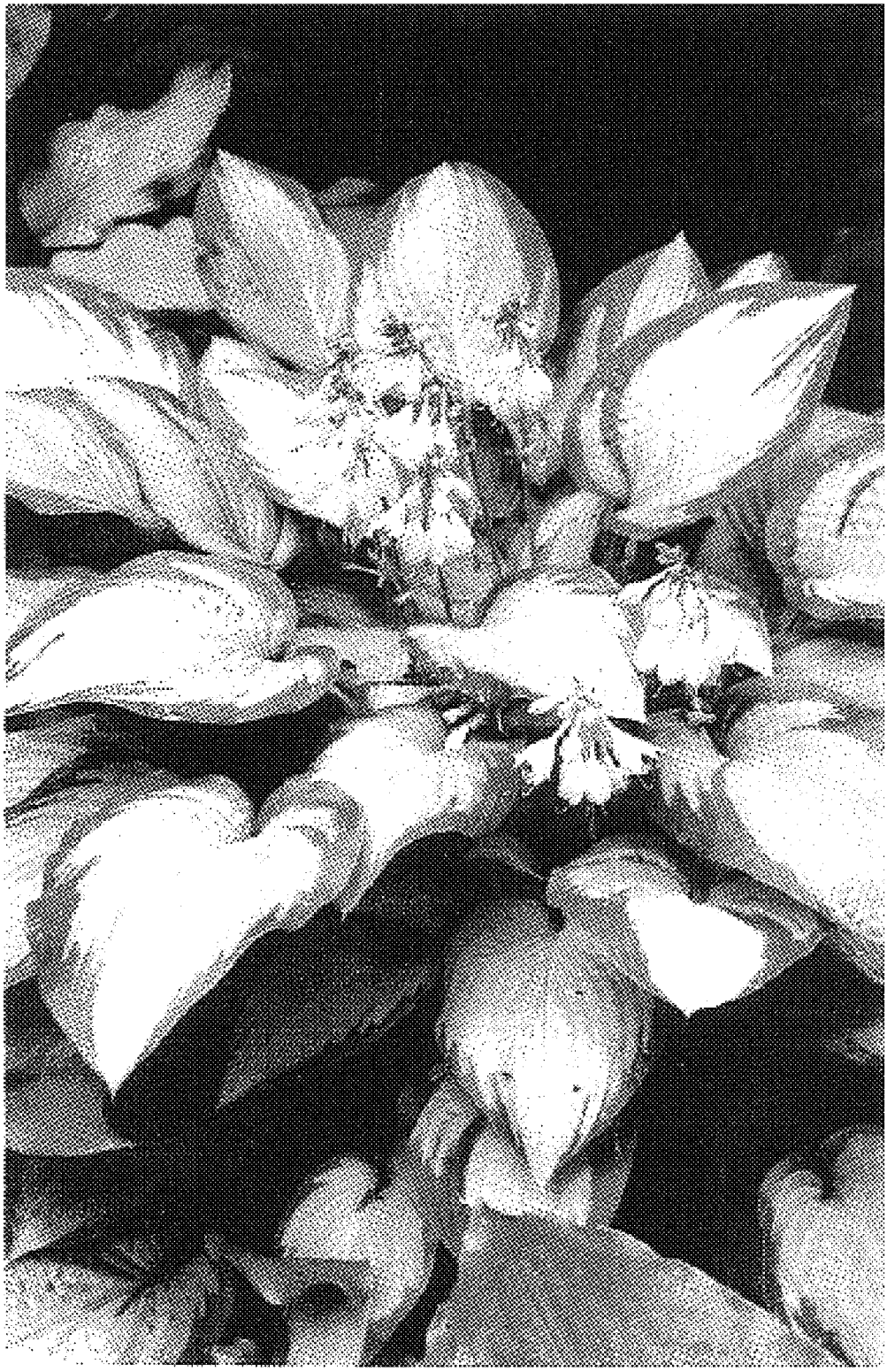
FIG. 5 shows a late season flowering *Hosta* plant (Paul's Glory) taken at the same time and location as the novel cultivar show in FIG. 4.

In the following description, color references are made to The Royal Horticultural Society Colour Chart except where general terms of ordinary dictionary significance are used. The following observations and measurements describe four-year old plants, as depicted in the accompanying color photographs, which were grown outdoors in plastic containers in Boonton, N.J., United States of America.

Botanical classification: *Hosta hybrida* 'Orange Marmalade'.

Parentage: Naturally occurring whole plant mutation of *Hosta* cultivar 'Paul's Glory'.

Propagation:

*Method.*—By division and tissue culture.

Plant description:

*Plant shape.*—Compact, open mound, dome-shaped.

*Growth habit.*—Initially upright when young, leaves becoming outwardly arching.

*Culture.*—Light to medium shade in moist soil.

*Plant type.*—Herbaceous perennial.

*Plant height.*—About 17 inches from the soil level to the top of the leaf plane.

*Plant diameter.*—About 32 inches.

*Vigor and growth rate.*—Moderate.

*Disease resistance.*—No known particular resistance or susceptibility to disease known to *hostas* observed.

*Foliage description.*—Leaves basal, simple and generally symmetrical. leaf shape: Broadly ovate to ovate. Apex: Acute. Base: Rounded to cordate. Leaf margin: Entire. Leaf texture: Glabrous above and below, moderate to heavy substance, and moderate puckering of mature leaves moderate to heavy substance means, upon rubbing the leaf between the forefinger and thumb, the leaves are stiff, able to hold their shape well, resist wind and pest damage, and usually maintain a good appearance throughout the growing season. Leaf size: Length: About 9 inches. Width: About 6 inches. Venation pattern: Campylodrome with 10 pairs of veins. Leaf color: Early season foliage: Upper Surface of Leaf: Yellow Centers: 12B. Margins: Green 137A, margins being ½ to ¾ of an inch wide. Streaks of yellow 9C to 9B and Yellow-green 144A may extend from margin into center. Lower surface of Leaf: Centers: Yellow 12C. Margins: Green 137B. Mid-season foliage: Upper surface of Leaf: Centers: Yellow 9D. Margins: Green 135A, margins being ½ to ¾ of an inch wide. Streaks of yellow 9C to 9B and yellow green 144A may extend from the margin to the center. Lower surface of Leaf: Centers: Yellow 9D Margins: Green 135B. Late season foliage: Upper surface of Leaf: Centers: Yellow: 11C. Margins: Green 136A, margins being ½ to ¾ of an inch wide. A third color, Yellow-green 153B, is present between the margin and center. Lower surface of Leaf: Centers: Yellow 11C Margins: Green 136B.

*Petiole description.*—Length: About 35 centimeters. Diameter: About 1.3 centimeters. The petiole of a young leaf has a central region having yellow green color, 144D and a margin about 1 millimeter wide, Green, 135A in color. The petiole of a mature leaf has a central region having a Yellow-green color 145B, and a margin, about 1 millimeter wide, Green 136A to 137A, in color.

Bud description:

*Shape.*—Ballon-shaped increases in size until day before opening.

*Bud length.*—About 4.5 centimeters.

*Bud diameter.*—About 1.5 centimeters.

*Bud color.*—Light lavender 76D; tips 72C.

Flower description:

*Bloom period.*—Mid-July to mid-August in Boonton, N.J.

*Fragrance.*—No observed fragrance.

*Flower arrangement.*—Raceme of numerous single flowers comprised of six tepals. There is one raceme per plant. The number of flowers per raceme is about 30 with each flower lasting approximately one day.

*Flower shape.*—Funnel-shaped.

*Flower size.*—Length: About 5.5 centimeters. Diameter of corolla: About 4 centimeters.

*Flower color.*—Light lavender, about 76D with the midrib of the tepals lavender, about 72D.

*Perianth.*—Arrangement: Three interior and three exterior tepals; fused. Tepal length: About 3.2 centimeters. Tepal width: About 1.2 centimeters. Tepal color: Upper Surface: Light lavender 76D with tepal midrib lavender, 72D. Lower Surface: Light lavender about 76D midrib lavender 72C. The tepals are ovate in shape with an acute apex. Margin is often transparent on the interior tepals, less so or not transparent on exterior tepals. Tepals are ribbed.

*Floral bracts.*—Arrangement: At pedicel base. Length: About 3.5 centimeters. Width: About 1.2 centimeters. Shape: Lanceolate, keel-shaped. Color: Yellow 11C with a Green margin, 137A. There is one bract per flower.

*Pedicel.*—Length: About 4 millimeters. Angle: Horizontal to about 40 degrees from vertical; bent with the weight of flower. Color : 145A.

*Scape.*—Length: About 26 inches. Aspect: Upright Texture: Smooth, glaucous. Color: Green 142B.

*Reproductive organs.*—Stamens: Quantity: Six; dorsifixed. Filament length: About 5.8 centimeters. Filament color: Green-white 157D. Anther size: About 3 millimeters by 1 millimeter. Anther color: Purple 93A. Pollen Amount: Moderate. Pollen color: Yellow-orange 17B. Pistils: Quantity: One. Pistil length: About 5.5 centimeters. Style Length: About 5.3 centimeters. Style color: 157D. Stigma color 157D. Ovary Length: About 7 millimeters. Ovary Color: 144B.

Seed development:

*Seed pod.*—Arrangement: Three carpeled capsule, approximately 8 to 10 seeds per carpel. Length: About 3 centimeters. Diameter: About 1 centimeter. Color: Yellow-green, 146C.

*Seeds.*—Arrangement: Single-winged. Length: About 1 centimeter. Color. Black.

Root development:

*Root description.*—Fleshy, typically about ⅛ in diameter and 12 to 16 inches long.

*Root development.*—Tissue culture liners potted in 1 quart pots in late spring and grown outdoors in commercial production shade structures under irrigation in Chapel Hill, N.C., United States of America, will fill the pot with roots in approximately 60 days.

I claim:

1. A new and distinct cultivar of *Hosta* plant named, 'Orange Marmalade', as illustrated and described.

* * * * *